US007949095B2

(12) United States Patent  (10) Patent No.: US 7,949,095 B2
Ning et al.  (45) Date of Patent: May 24, 2011

(54) METHODS AND APPARATUS FOR DIFFERENTIAL PHASE-CONTRAST FAN BEAM CT, CONE-BEAM CT AND HYBRID CONE-BEAM CT

(75) Inventors: Ruola Ning, Fairport, NY (US); Weixing Cai, Rochester, NY (US)

(73) Assignee: University of Rochester, Rochester, NY (US)

( * ) Notice: Subject to any disclaimer, the term of this patent is extended or adjusted under 35 U.S.C. 154(b) by 0 days.

(21) Appl. No.: 12/705,085

(22) Filed: Feb. 12, 2010

(65) Prior Publication Data

US 2010/0220832 A1  Sep. 2, 2010

Related U.S. Application Data

(60) Provisional application No. 61/156,642, filed on Mar. 2, 2009.

(51) Int. Cl.
*G01N 23/04* (2006.01)
(52) U.S. Cl. .............................. 378/62; 378/4
(58) Field of Classification Search ............... 378/4, 62
See application file for complete search history.

(56) References Cited

U.S. PATENT DOCUMENTS

| | | | |
|---|---|---|---|
| 5,375,156 A | 12/1994 | Kuo-Petravic et al. | |
| 5,802,137 A | 9/1998 | Wilkins et al. | |
| 5,999,587 A | 12/1999 | Ning et al. | |
| 6,018,564 A | 1/2000 | Wilkins et al. | |
| 6,047,042 A | 4/2000 | Khutoryansky et al. | |
| 6,075,836 A | 6/2000 | Ning | |
| 6,298,110 B1 | 10/2001 | Ning | |
| 6,477,221 B1 | 11/2002 | Ning | |
| 6,480,565 B1 | 11/2002 | Ning | |
| 6,504,892 B1 | 1/2003 | Ning | |
| 6,618,466 B1 | 9/2003 | Ning | |
| 6,987,831 B2 | 1/2006 | Ning | |
| 2005/0226376 A1* | 10/2005 | Yun et al. ................. 378/62 |
| 2005/0286680 A1 | 12/2005 | Momose | |
| 2006/0039532 A1 | 2/2006 | Wu et al. | |
| 2006/0094950 A1 | 5/2006 | Ning | |
| 2007/0183558 A1* | 8/2007 | Hempel .................. 378/4 |

(Continued)

FOREIGN PATENT DOCUMENTS

CN 101622526 A 1/2010
WO 2007100823 A2 9/2007

OTHER PUBLICATIONS

Jiang et al., X-ray Phase-Contrast Imaging with Three 2D Gratings, International Journal of Biomedical Imaging Volume, 2008, Article ID 827152, pp. 1-8.*
Huang et al., Large phase-stepping approach for high-resolution hard X-ray grating-based multiple-information imaging, Optics Express, Apr. 2010, pp. 10222-10229.*
T Weitkamp, A Diaz, C David, F Pfeiffer, M Stampanoni, P Cloetens and E Ziegler, "X-ray phase imaging with a grating interferometer," Opt. Express 2005; 13(16):6296-6304.

(Continued)

*Primary Examiner* — Edward J Glick
*Assistant Examiner* — Alexander H Taningco
(74) *Attorney, Agent, or Firm* — Blank Rome LLP (57) ABSTRACT

A device for imaging an object, such as for breast imaging, includes a gantry frame having mounted thereon an x-ray source, a source grating, a holder or other place for the object to be imaged, a phase grating, an analyzer grating, and an x-ray detector. The device images objects by differential-phase-contrast cone-beam computed tomography. A hybrid system includes sources and detectors for both conventional and differential-phase-contrast computed tomography.

62 Claims, 9 Drawing Sheets

U.S. PATENT DOCUMENTS

2007/0183559 A1    8/2007   Hempel
2007/0183582 A1*   8/2007   Baumann et al. ............. 378/145
2007/0274435 A1*  11/2007   Ning et al. ........................ 378/4
2010/0091947 A1*   4/2010   Niu et al. ......................... 378/63

OTHER PUBLICATIONS

G Faris and R Byer, "Three-dimensional beam-deflection optical tomography of a supersonic jet," Appl. Opt. 1988; 27(24):5202-5212.

* cited by examiner

METHODS AND APPARATUS FOR DIFFERENTIAL PHASE-CONTRAST FAN BEAM CT, CONE-BEAM CT AND HYBRID CONE-BEAM CT

REFERENCE TO RELATED APPLICATION

The present application claims the benefit of U.S. Provisional Patent Application No. 61/156,642, filed Mar. 2, 2009, whose disclosure is hereby incorporated by reference in its entirety into the present disclosure.

STATEMENT OF GOVERNMENT INTEREST

This invention was made with government support under Grant Nos. R01 9 HL078181 and 4 R33 CA94300 awarded by National Institutes of Health. The government has certain rights in the invention.

FIELD OF THE INVENTION

The present invention is directed to cone-beam computed tomography (CT) imaging and more particularly to phase-contrast cone-beam CT for such uses as breast imaging.

DESCRIPTION OF RELATED ART

According to the National Cancer Institute, one out of eight women will be diagnosed with breast cancer in their lifetime. And while a reduction in mortality from breast cancer is evident in published reports, each year 40,000 women will die of the disease.

The optimal breast imaging technique detects tumor masses when they are small, preferably less than 10 mm in diameter. It is reported that women with mammographically detected invasive breast carcinoma 1-10 mm in size have a 93% 16-year survival rate. In addition, as the diameter of the tumor at detection decreases, the probability of metastasis declines sharply. If a breast tumor is detected when it is 10 mm or less, the probability of metastasis will be equal to 7.31%. If a 4 mm carcinoma is detected, the metastatic probability will be decreased by more than a factor of 10, to 0.617%.

Although mammography, which on average can detect cancers ~12 mm in size, is the most effective tool for the early detection of breast cancer currently available, has relatively low sensitivity to small breast cancers (under several millimeters). Specificity and the positive predictive value of mammography remain limited owing to structure and tissue overlap. Limited sensitivity and specificity in breast cancer detection of mammography are due to its poor contrast detectability, which is common for all types of projection imaging techniques (projection imaging can only have up to 10% contrast detectability), and mammography initially detects only 65-70% of breast cancers. The sensitivity of mammography is further reduced to as low as 30% in the dense breast. Digital mammography (DM) was developed to try to overcome the limitations inherent in screen-film mammography (SFM) by providing improved contrast resolution and digital image processing; however, a large scale clinical trial, the Digital Mammographic Imaging Screening Trial (DMIST), showed that the rates of false positives for DM and SFM were the same.

The relatively low specificity of mammography leads to biopsy for indeterminate cases despite the disadvantages of added cost and the stress it imposes on patients. Nearly 80% of the over one million breast biopsies performed annually in the U.S. to evaluate suspicious mammographic findings are benign, burdening patients with excessive anxiety and the healthcare system with tremendous cost. There is a need for more accurate characterization of breast lesions in order to reduce the biopsy rate and the false-positive rate of pre-biopsy mammograms.

To address the mammography limitations as indicated above, we have previously developed a cone beam breast CT (CBBCT). Briefly, the major features of the prototype include a horizontal, ergonomically designed patient table with a modular insert to optimize coverage of the uncompressed breast, including the chest wall; wide openings (1 m) on each side of the patient table for easy access to the breast for positioning and potentially good access for imaging-guided biopsy and other procedures without significantly changing the basic platform; and slip-ring technology that facilitates efficient dynamic contrast imaging studies and angiogenesis imaging in the future.

The results of a phantom studies indicate that CBBCT can achieve a spatial resolution up to ~2.8 lp/mm, allowing detection of a 2 mm carcinoma and the microcalcifications ~0.2 mm in size for an average size breast (~13 cm in diameter at the chest wall) with a total dose of ~5 mGy. This dose is less than that of a single mammography exam, assuming two views are required for each breast. The image quality of CBBCT for visualizing breast tissues, breast tumors and calcifications is excellent, and coverage of the breast, including the chest wall region, is at least equivalent to mammography. Visualization of major blood vessels is very good without using a contrast agent.

Ultrasound (US) is used diagnostically to distinguish fluid versus solid masses and for localization and biopsy. Lately, it has been investigated with some success to determine benign versus malignant masses through a US exam. US is a low spatial resolution study, has severe limitations in visualizing and characterizing calcifications and is highly dependant on operator skill Intravenous dynamic contrast enhanced breast MRI (CEBMRI) currently is the only tool that provides functional information to aid in the diagnosis of breast cancer. The CEBMRI study has a high negative predictive value and near 100% sensitivity for invasive breast cancer and serves as a valuable adjunctive modality in managing the breast cancer patient once cancer has been diagnosed by other means. Because it is a tomographic study, it is currently the only breast imaging modality that is FDA approved and can truly be compared to CBBCT. CEBMRI is fully dependent on contrast resolution arising from intravenous contrast agents and the neovasculature associated with tumors. The difference in CEBMRI and all other imaging is that the image reflects contrast enhancement of vasculature rather than the actual breast anatomy. Although CEBMRI has a high sensitivity for invasive cancers, current techniques may be limited in detecting ductal carcinoma in situ (DCIS). CEBMRI is not able to distinguish calcifications and the proposed non-neovasculature involvement with DCIS, which are evident in up to 50% of breast cancers not associated with a mass.

Digital breast tomosynthesis (DBT) presently under development aims to mitigate the effect of overlapping structures. Though a measure of success has been achieved, DBT is fundamentally limited by its constraints in projection geometry; the tomographic slice is not well defined, which can cause a loss of resolution in the axial direction that affects visualization of subtle features, such as amorphous microcalcifications. CBBCT can provide isotropic high-resolution imaging of the entire breast in a more complete tomographic approach compared to other modalities, with out breast compression. It is likely to be of particular value for imaging dense breasts and breasts with implants.

As discussed above, compared to mammography including digital mammography, CBBCT has made significant advancements in detecting breast cancer. However, to accurately characterize breast tumors and calcifications and significantly reduce the biopsy rate and false positive rate of breast biopsy, it is desirable that the CBBCT should achieve a comparable spatial resolution of the pathology image which is the gold standard for breast cancer diagnosis. The requirement of multifold increase in spatial resolution will mandate increasing the radiation dose over 100 times in order to maintain the same contrast-to-noise ratio (CNR) as current CBBCT. For example, if the spatial resolution is required to be increased from 2 lp/mm to 25 lp/mm, to maintain a clinical acceptable CNR, the dose level would be increased from ~6 mGy for an average sized breast with the current CBBCT ~186 times to 1.1 Gy. This dose increase is clinically prohibited.

The following references are considered to provide background information:
1. T Weitkamp, A Diaz, C David, F Pfeiffer, M Stampanoni, P Cloetens and E Ziegler, "X-ray phase imaging with a grating interferometer," Opt. Express 2005; 13(16):6296-6304.
2. G Faris and R Byer, "Three-dimensional beam-deflection optical tomography of a supersonic jet," Appl. Opt. 1988; 27(24):5202-5212.

SUMMARY OF THE INVENTION

It is therefore an object of the invention to allow an increase in spatial resolution without increasing the dose to a prohibited level.

It is therefore other object of the invention to allow substantially reduce x-ray radiation dose to a patient without reducing spatial resolution and contrast to noise ratio.

To achieve the above and other objects, the present invention is directed to a system and method for breast imaging or other purposes (for example, vascular imaging, pediatric cone beam CT, whole body CT imaging and interventional cone beam CT), using x-ray differential phase-contrast cone beam CT. X-ray phase contrast cone beam CT and cone beam CT imaging as an emerging new technology will potentially achieve the spatial resolution level up to 25 lp/mm (20 μm voxel size) while maintaining an x-ray dose similar to that of the current CBBCT and mammography. In addition, since x-ray phase contrast imaging is dependent on the principles of refraction and interference of x-ray waves, more subtle information can be detected by retrieving the phase coefficients than that possible with conventional attenuation-based x-ray imaging techniques retrieving attenuation coefficients.

Conventional attenuation-based CT and cone beam CT are quite efficient in distinguishing absorption contrast between soft and hard tissues that have very different linear attenuation coefficients. However, when imaging soft tissues including breast tissues, the low absorption contrast differences of the breast structures (benign and malignant) limit its performance. Phase-contrast techniques are expected to provide an alternative way for soft tissue imaging. Unlike the principle of absorption contrast, phase-contrast imaging originates from the wave nature of x-rays, where refraction and diffraction need to be considered. As an electromagnetic wave, the x-ray is usually characterized by its wavelength, amplitude and phase. When it goes through a medium, its amplitude is attenuated, and its phase is shifted. In x-ray technology, the refraction index n of a material is usually expressed as a complex number $n=1-\delta+i\beta$. The imaginary part $\beta$ contributes to the attenuation of the amplitude, and the real part $\delta$ is responsible for the phase shift. It has been shown theoretically and experimentally that $\delta$ is usually more than $10^3$ times larger than $\beta$. Therefore, a phase contrast imaging technique will potentially provide 1000 times higher object contrast than attenuation-based CT and cone beam CT techniques.

In the past decade, various phase-contrast techniques have been developed to manifest the contrast of $\delta$, almost all of which depend on micro-focus x-ray tubes or synchrotron radiation that are not practical for widespread clinical applications. Recently, a new phase contrast imaging technique called the differential phase-contrast (DPC) technique has been proposed, which is a grating-based interferometry method. A high power hospital-grade x-ray tube with a wide polychromatic spectrum and high output x-ray power can be used to acquire DPC images. However, it has not previously been used in the context of the present invention.

Related systems and methods are disclosed in the following U.S. patents: U.S. Pat. No. 6,987,831, "Apparatus and method for cone beam volume computed tomography breast imaging"; U.S. Pat. No. 6,618,466, "Apparatus and method for x-ray scatter reduction and correction for fan beam CT and cone beam volume CT"; U.S. Pat. No. 6,504,892, "System and method for cone beam volume computed tomography using circle-plus-multiple-arc orbit"; U.S. Pat. No. 6,480,565 "Apparatus and method for cone beam volume computed tomography breast imaging"; U.S. Pat. No. 6,477,221, "System and method for fast parallel cone beam reconstruction using one or more microprocessors"; U.S. Pat. No. 6,298,110, "Cone beam volume CT angiography imaging system and method"; U.S. Pat. No. 6,075,836, "Method of and system for intravenous volume tomographic digital angiography imaging"; and U.S. Pat. No. 5,999,587, "Method of and system for cone-beam tomography reconstruction," whose disclosures are all incorporated by reference in their entireties into the present disclosure. The techniques disclosed in those patents can be used in conjunction with the techniques disclosed herein.

BRIEF DESCRIPTION OF THE DRAWINGS

Preferred embodiments of the present invention will be set forth in detail with reference to the drawings, in which.

DETAILED DESCRIPTION OF THE PREFERRED EMBODIMENT

Preferred embodiments of the present invention will be set forth in detail with reference to the drawings, in which like reference numerals refer to like elements or steps throughout.

Figure 1A:
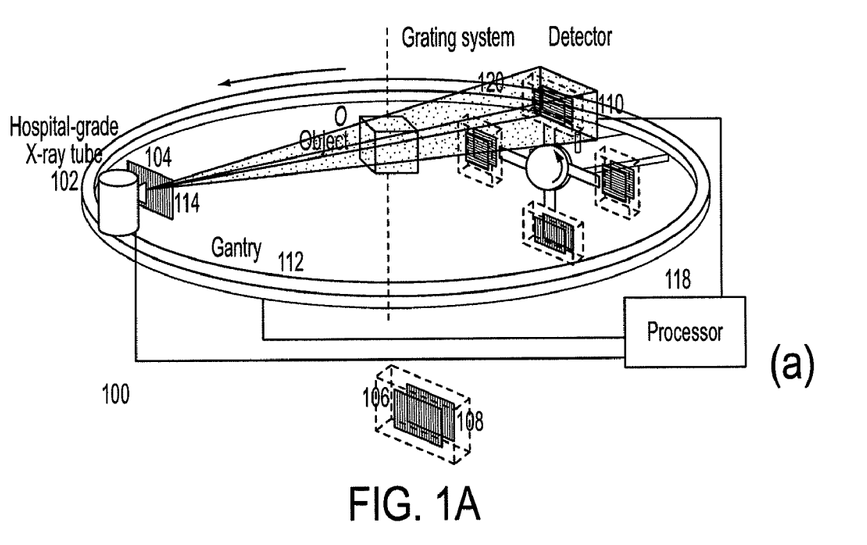
FIGS. 1A and 1B are schematic diagrams showing a system according to a first preferred embodiment.
Figure 1B:
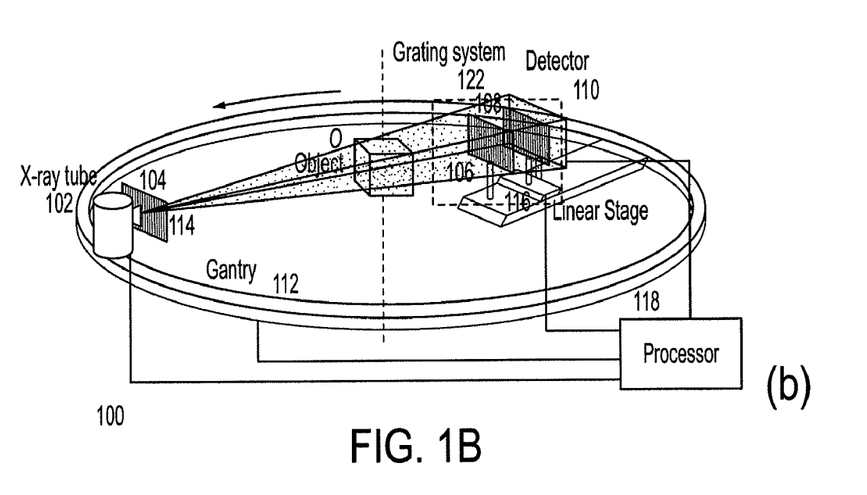

A first preferred embodiment is directed to a differential phase-contrast cone-beam CT system (DPC-CBCT) for in vivo clinical imaging using the differential phase-contrast imaging technique. As shown in FIGS. 1A and 1B, such a DPC-CBCT system 100 includes a hospital-grade x-ray tube 102 with a source grating 104, a high-resolution detector 110 and a grating system mounted on a gantry 112. To ensure the mechanical precision and stability, the grating system can be designed either as the grating system 120 in FIG. 1A or as the grating system 122 in FIG. 1B. The purpose of grating system is to produce different phase steps that are defined as relative displacements between the phase grating 106 and the analyzer grating 108 in the direction perpendicular to grating lines. Grating system 120 is composed of several branches and at each branch, a phase grating 106 and an analyzer grating 108 are fixed. The relative displacement between the phase grating 106 and the analyzer grating 108 ranges from a small fraction of the period of the analyzer grating 108 to one grating period across different branches. Grating system 122 uses only one phase grating 106 and one analyzer grating 108, and a motor-driven stage 116 moves either the analyzer grating 108 or the phase grating 106 to produce different phase steps. The object O will be kept stationary while the gantry will be rotating to take images during a scan. A processor 118 controls the operations of the system and analyzes the data.

The DPC technique is able to produce one-dimensional or two-dimensional spatial coherence by applying an absorption grating (the source grating 104) to a high power x-ray tube 102 that has a focal spot size of hundreds of microns and a high x-ray output power (>10 kW). The line patterns 114 made of high atomic number materials of the source grating 104 can absorb almost all x-ray photons impinging on them while the grooves in between let all the x-ray photons pass through. The width of the grooves is designed to be comparable to the focal spot size of a micro-focus x-ray tube. Thus the source grating divides a large focal spot x-ray source into several narrow line sources. Each of these line sources is able to produce sufficient spatial coherence at the direction perpendicular to the lines, while they are mutually incoherent. When proper parameters are chosen, these line sources contribute constructively in the imaging process. In a similar manner, the grating pattern can be designed as a matrix of small openings and each opening functions as a point source that is able to individually provide sufficient coherent length in both dimensions but mutually incoherent. Combined with other two-dimensional gratings, such a system can produce phase information equally in both directions.

The phase-stepping algorithm [1] is used to calculate each DPC image, the physical principle of which is briefly explained as following: The phase grating 106 shows negligible absorption but substantial phase shift, dividing the x-ray beam into two first diffraction orders. The refracted beams then interfere and form periodical fringes at an integer or fractional Talbot distance where the analyzer grating 108 is placed. The period of the analyzer grating is chosen to be the same as the period of the fringes. If the incident x-ray beam encounters an object before it reaches the phase grating, its wavefront will be perturbed by the object, leading to local displacement of the fringes. To retrieve the encoded phase information, the most efficient and robust method now is the phase stepping algorithm. An x-ray detector with a pitch larger than the diffraction fringe period can be used to record the intensity images, which removes the restriction of an ultrahigh detector resolution that has a pitch even smaller than the diffraction fringes. When the analyzer grating or the phase grating is stepped increasingly by a fraction of the grating period, the detected intensity value of any pixel in the detector is modulated by the position of the stepped grating, and this modulation shows the same period as the analyzer grating. If the modulation function is transformed into Fourier domain, then the complex angle of the first Fourier component is the first derivative of phase at this pixel. The DPC image of an object acquired in this way is a raw DPC image. Usually the background phase distribution due to the non-uniformity of grating system is required by the same process without an object in place, and the true DPC image of the object is acquired by subtracting the background phase distribution from the raw DPC image. The whole procedure is show in FIG. 2. It should be noted that the background information can be pre-stored for the background correction for a given DPC system, and therefore it is not necessary to be acquired for every scan. Theoretically, at least two sampling points are needed to represent a periodic function, and thus at least two phase steps are needed to perform the phase stepping algorithm. In practice, three or more sampling points are needed to avoid aliasing artifacts. The grating system 122 is a straightforward implementation of the phase-stepping algorithm when precise mechanical accuracy and stability can be achieved during a DPC-CBCT scan. The grating system 120 is a mechanically robust implementation of the phase-stepping algorithm. Considering the requirements of mechanical accuracy and stability of the order of sub-micron, it is difficult to keep such a precision in stepping either grating when the gantry is rotating at a high speed. Therefore, we propose to use a novel multiple grating sets where the relative position of the phase grating and the analyzer grating in each set is fixed and is corresponding to a phase step. Instead of stepping either grating, it is just required to rotate the dial of the grating system to successively align the grating set of each branch with the optical axis of the x-ray beam to acquire an intensity image for each phase step, and these intensity images are then processed to calculate the DPC image using the method described above.

Figure 2:
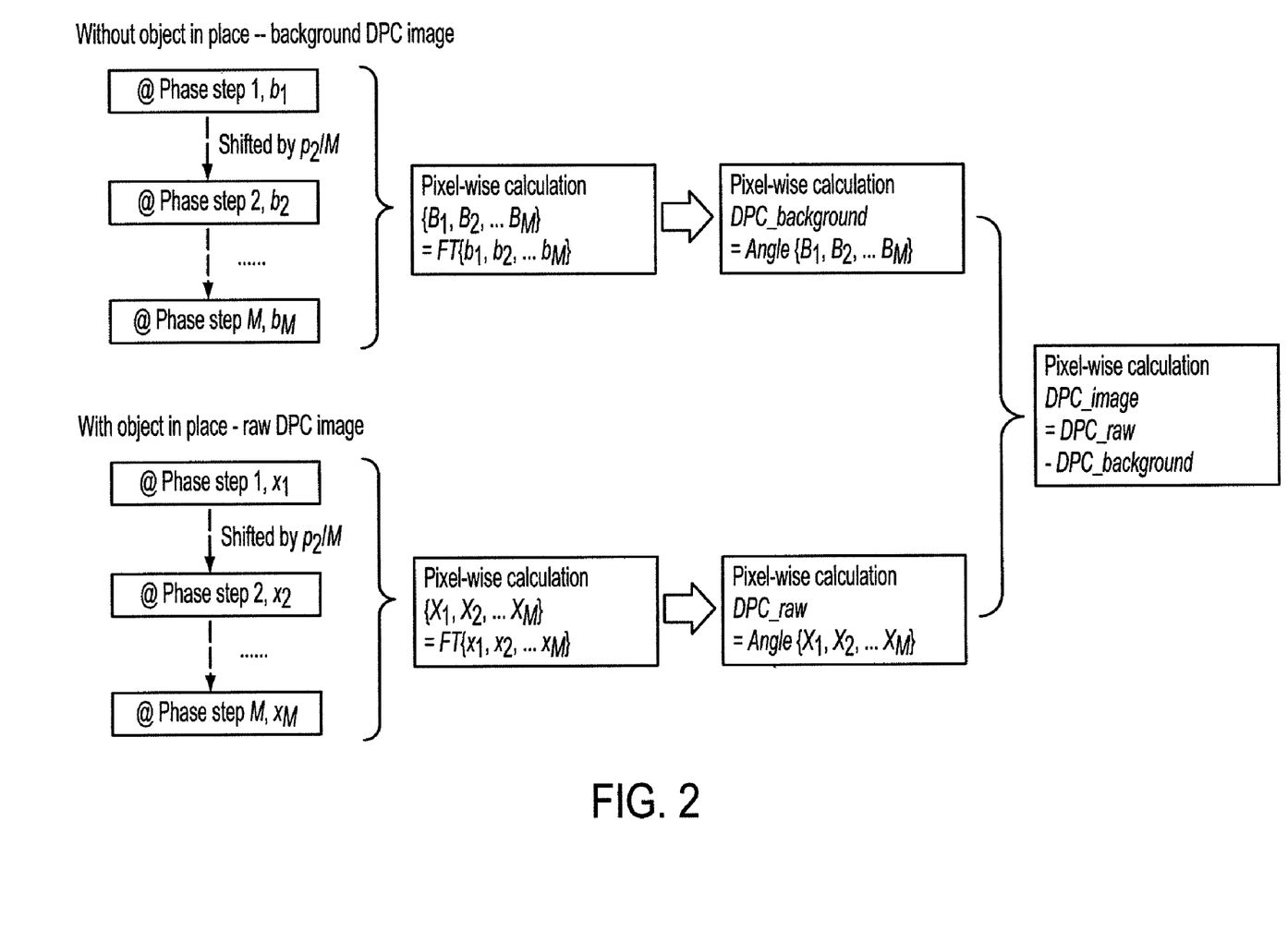
FIG. 2 demonstrate the phase-stepping algorithm.

The DPC images acquired from all view angles will be directly used for reconstruction instead of calculating the line integrals of phase coefficient first from the DPC images. Considering that the cone angle of the DPC-CBCT system is small, the parallel beam approximation can be applied for tomographic reconstruction, and a filtered backprojection (FBP) algorithm with Hilbert filtering can be used [2]. The DPC images are row-wisely filtered using the Hilbert filter, and then are backprojected into the object space to calculate the 3-D distribution of the linear phase coefficient. When the object is fully covered by the x-ray beam at all view angles (no transverse truncation), the reconstruction result is accurate up to a constant. The reconstruction constant can be easily determined by setting the phase coefficient of surrounding air to zero. In the case of volume-of-interest (VOI) imaging where truncation occurs, this reconstruction method also works, but the image quality will be degraded by the background trend, and the reconstruction constant has to be determined using prior knowledge of the object. Besides, backprojection-filtration (BPF) algorithms can be modified for DPC-CBCT reconstruction because a differentiation operation is usually performed before backprojection while the DPC image is very similar to the intermediate result after the differentiation operation. This type of algorithm also has a good capability to handle severe truncations. The procedure of DPC-CBCT imaging using a typical BPF reconstruction comprises the same methods to obtain DPC images, and the only difference is the reconstruction method. The major steps are: (a) acquire raw intensity data from all view angles; (b) compute DPC images using the phases-stepping algorithm from the intensity data as shown in FIG. 2; (c) backproject the DPC images to the object space from all view angles; and (d) filter the backprojected data using desired filter(s) along specified direction(s).

Figure 3A:
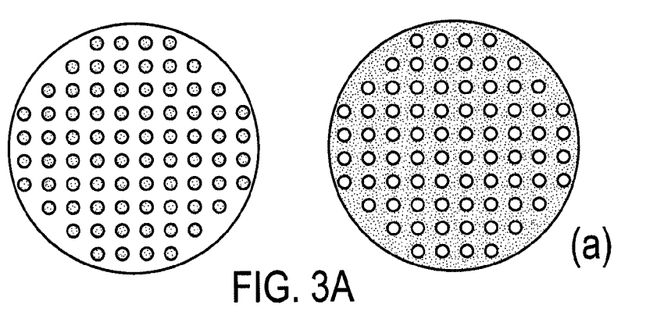
FIGS. 3A and 3B show designs of preferred two-dimensional grating embodiments.
Figure 3B:
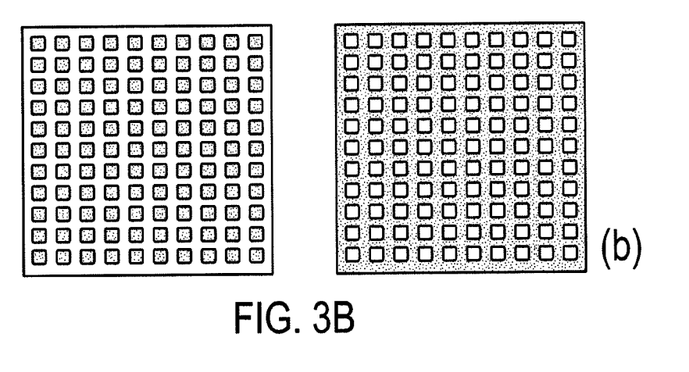

In this disclosure the one-dimensional grating system with the corresponding scanning protocol and reconstruction algorithm is discussed in details. It should be noted that it is straightforward to extend the one-dimensional grating system into a two-dimensional system where the source grating is composed of multiple point sources while the phase grating and the analyzer grating are composed of two-dimensional matrices. Some of the possible embodiments are shown in FIGS. 3A and 3B. The phase-stepping algorithm should be performed in preferred directions (x, y, diagonal and etc) to extract the phase contrast equally in both x and y directions. A modification should be carried out for the cone beam reconstruction algorithm to deal with the phase gradient in both directions.

Major parameters of the proposed DPC-CBCT system are listed in Table 1. A hospital-grade x-ray is used for the DPC-CBCT system. The x-ray tube has a focal spot size of 0.05 mm to 2 mm and an output power of several kilowatts to tens of kilowatts. It will operate at 10 kVp to 150 kVp. Generally it can be any kind of diagnostic imaging x-ray radiation sources, including mammography tubes, angiography tubes, CT tubes and other general purpose radiographic tubes, depending on the clinical applications.

TABLE 1

| Major system parameters | |
|---|---|
| Focal spot size | 0.05 mm-2 mm |
| Peak voltage | 10 kVp-150 kVp |
| Detector pixel size | 10 µm-1000 µm |
| Detector frame rate | 0.5 fps-1000 fps |
| Detector dimensions | 3 cm × 3 cm-50 cm × 50 cm |
| Gantry rotation speed | >0.5 RPM |

A two-dimensional detector is used for the DPC-CBCT system. Unlike other phase-contrast imaging techniques, there is no strict requirement for an ultra high resolution detector, and the detector resolution can be ~10 µm-1000 µm, determined by the applications and expected image resolution. The frame rate of the detector is 0.5 frames per second (fps) to 120 fps for different image acquisition protocols.

The source grating is mounted as close to the focal spot as possible for the best field of view. It divides the x-ray beam into many line sources, and the width of each line source is less than 50 µm. The phase grating is mounted right behind the object and yields a phase difference of PI between grooves and ridges. The period of the phase grating is 2 µm to 8 µm. The analyzer grating is mounted right at the surface of the detector and it attenuates x-rays to 20% to 80% at grooves by strongly attenuation materials. The period of the analyzer grating is the same or half of that of the phase grating, depending on the distance between the two gratings, which can be fractional Talbot distances or integer Talbot distances. The distance between the source grating and the phase grating and the distance between the phase grating and the analyzer grating determine the period of the source grating, which is usually 60 µm to 200 µm. The sizes of gratings are designed to cover the field of view for the specific applications of the DPC-CBCT system. Major grating parameters are listed in Table 2. A possible variation would use two-dimensional phase contrast gratings. It should be noted that such a grating design is ideal for parallel x-ray beam or an x-ray beam with small cone angle as the grating grooves are parallel. When a larger cone angle (>5 deg) is used, it would be better to use focused gratings that is designed and fabricated with consideration of the diverging x-ray beam.

TABLE 2

| Major grating parameters | | | |
|---|---|---|---|
| | Source grating 104 | Phase grating 106 | Analyzer grating 108 |
| Grating pitch p (µm) | 60-200 | 2-8 | Same or half that for phase grating 106 |
| Groove height t (µm) | 40-200 | 10-50 (phase shift of PI) | 10-50 |
| Duty cycle | Line width <50 µm | 50% | 50% |

Figure 4A:
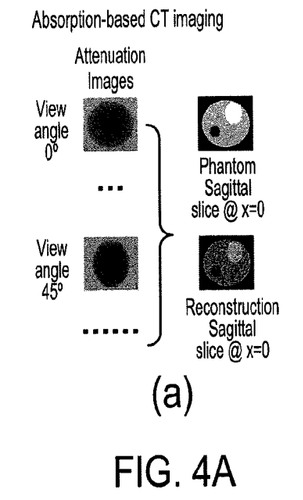
FIGS. 4A and 4B compare the imaging process of a DPC-CBCT and a conventional absorption-based CBCT.
Figure 4B:
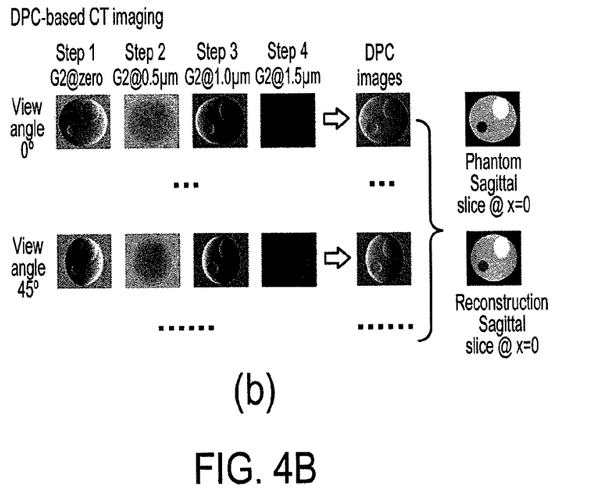

The x-ray tube, detector and grating system are mounted on a rotation gantry that can achieve a speed of 0.5 revolutions per minute (RPM) to 60 RPM or larger. The patient is kept stationary during a scan. FIGS. 4A and 4B compare computer simulation images of a simple numerical phantom using the attenuation technique and the DPC technique with the same total exposure level and reconstructed spatial resolution. The numerical phantom is composed of three ellipsoids and is placed at the center of the scanning plane. The attenuation-based CBCT takes one intensity image at each view angle, and a sagittal slice is reconstructed as demonstrated in FIG. 4A. The DPC-based CBCT, as illustrated in the FIG. 4B, takes four intensity images at each view angle with the analyzer grating shifted by four different steps, and the exposure to each intensity image is a quarter of that of the attenuation-based image. The four intensity images are then processed to retrieve the DPC image using the principle of the phase-stepping algorithm. The same sagittal slice is then reconstructed from the set of DPC images. The phantom image of the same sagittal slice is shown for comparison. It can be observed that both DPC projection and reconstruction images show much higher CNRs than that of the absorption projection and reconstruction images. As expected, the measured contrast in the DPC-CBCT reconstruction image is about 1000 times higher than that of attenuation-based reconstruction, while the noise level of DPC-CBCT is 40 times higher than that of attenuation-based reconstruction. Then measured CNR is 28.2 in the DPC-CBCT reconstruction and 0.81 in the attenuation-based reconstruction, resulting in a CNR improvement of about 35 times. Thus with the same dose level and spatial resolution, DPC-CBCT imaging possibly provides an order of magnitude improvement CNR over that by attenuation-based CBCT. We have performed additional simulation to prove that with 25 lp/mm (20 µm) resolution and mammographic dose level, DPC-CBCT can achieve clinically acceptable CNR.

In the proposed DPC-CBCT technique, the data acquisition geometry is not limited to the circle orbit. The gantry can be controlled and moved by at least one motor to perform scans along various orbits, including a spiral geometry, a circle-plus-line geometry and a circle-plus-arc geometry.

Figure 5:
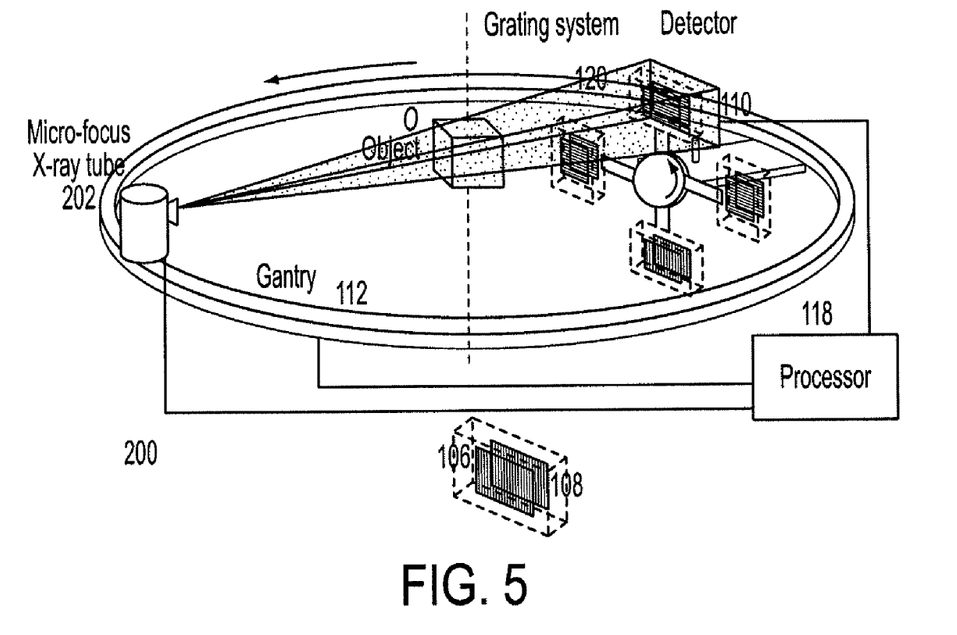
FIG. 5 is a schematic diagram showing a system according to a second preferred embodiment.
Figure 6:
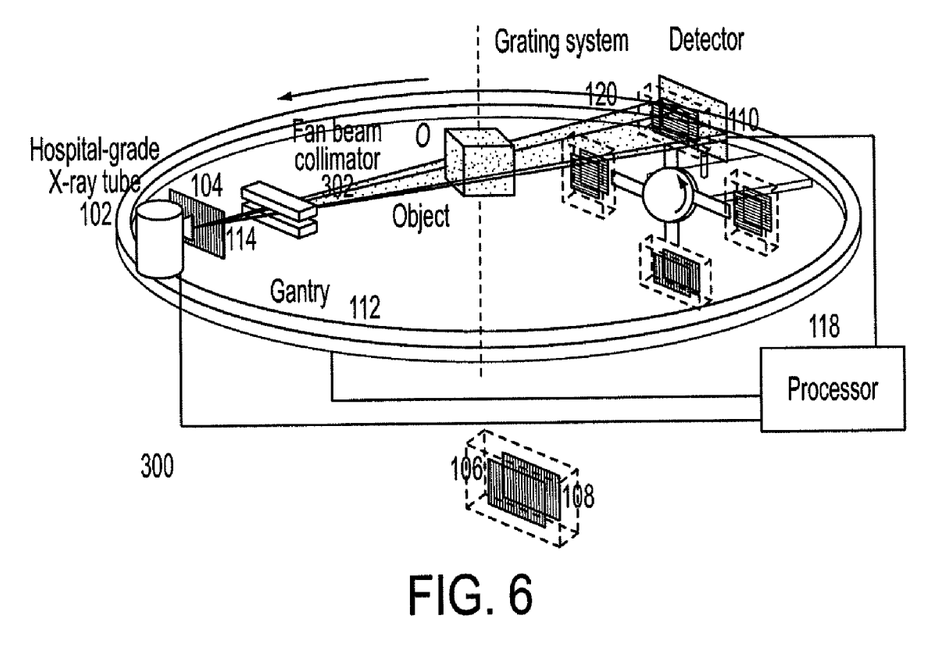
FIG. 6 is a schematic diagram showing a system according to a third preferred embodiment.

The second and the third preferred embodiments are two variations of the first preferred embodiment. The first variation is a micro-focus x-ray tube-based DPC-CBCT system 200 as shown in FIG. 5, which is the second preferred embodiment. A micro-focus tube 202 instead of a hospital-grade tube is used for the DPC-CBCT system 200. In this case, the source grating is not required as the micro-focus x-ray tube (with a focal spot size<0.05 mm) itself is able to provided sufficient coherence length for DPC imaging. The limitation of current micro-focus tubes is the weak output power (<100 watts). However, it is expected that the output power can be significantly increased if such techniques including liquid-metal-anode tube, plasma-driven tube and rotational anode tube are well developed in the future. The second variation is a fan beam DPC-CT system 300 as shown in FIG. 6, which is the third preferred embodiment. Considering that for the design of 1-D gratings only the phase contrast along the direction perpendicular to grating lines is manifested, the extent of the field-of-view along the direction of grating lines can be reduced without influencing the phase-contrast effect. A fan beam collimator 302 is used to shape the x-ray into a fan beam and the imaging principle is exactly the same as that for the DPC-CBCT system 100.

The present invention allows the implementation of a DPC-CBCT system to detect and characterize breast tumors and microcalcifications with a spatial resolution up to 25 lp/mm, which is comparable to that of pathology images and results in the significant reduction of biopsy rate. The following design considerations are involved. The first design consideration is to design and construct a coherent x-ray radiation source that combines the hospital-grade x-ray tube with a specially designed and constructed grating (104) to provide a stable coherent radiation source with 5 cm field of view (FOV) coverage or larger. The second design consideration is to fabricate high quality gratings with uniform microstructures to cover the proposed FOV. The third design consideration is to design and construct an appropriate 2D detector system which has ultra-high spatial resolution (~20 μm/detector cell), a high detective quantum efficiency (DQE), high dynamic range, minimal geometric distortion and excellent linearity. The fourth design consideration is to develop a practical DPC-CBCT data acquisition scheme along with accurate and efficient phase stepping algorithms and DPC-CBCT reconstruction algorithms. The fifth design consideration is to design and construct the proposed HBCT (hybrid breast CT) system (CBBCT plus DPC-CBCT) to ensure a targeting DPC-CBCT scan and proper coverage of the volume of interest.

As discussed above, the requirement for a phase contrast imaging system is that the incident x-ray beam should be spatially coherent to a certain degree, and it is possible to perform DPC-CBCT imaging using high power hospital-grade x-ray tubes with an attenuation grating. To meet this challenge, we propose to select a high-power mammography tube or general radiography tube with an anode power larger than 10 kW and couple it with a specially designed source grating 104 in FIG. 1, where the x-ray tube can be considered as being divided into many narrow line sources with width of 10-50 μm, and these line sources are individually spatially coherent in the direction perpendicular to grating grooves but mutually incoherent. With this design, the source is able to provide sufficient x-ray flux even with the strong attenuation of the source grating. The high aspect ratio (the ratio between groove height and groove width) of the grating 104 may affect the field of view, and it is important to mount the grating 104 as close to the focal spot as possible (preferably <1 cm) for larger FOV.

The gratings used for DPC-CBCT imaging will be fabricated using Micro-Electro-Mechanical Systems (MEMS) nanofabrication facilities, including photolithography, physical etching, chemical etching, deposition and electroplating. The major challenge is the high aspect ratio of the gratings (the ratio between groove height and width), which makes etching and electroplating difficult. For the phase grating and the analyzer grating, the aspect ratio can be as high as 15 to 40, which causes difficulties in etching with straight edges or growing gold into deep grooves. To solve this issue, a high-quality <110> orientated single crystal silicon substrate (Nova Electronic Materials, Flower Mound, Tex.) will be used that is highly selective in a preferred direction, with which it is easier to form sharp and deep edges by wet etching using potassium hydroxide (KOH). A nitride layer will be used as the mask and the atomic layer deposition (ALD) will be used to epitaxially grow the seed layer of gold. Next, electroplating will be used to grow the gold layer on top of the seed layer following its own crystal structure. Other elements with high atomic number like Pt, Hf or Ta can be used as well. Currently the standard large scale MEMS technique is limited to 2.5 inch×2.5 inch silicon wafers that just match the proposed field of view of around 5 cm×5 cm.

There is no strict limitation with detector resolution for the proposed DPC-CBCT system, and it can range from 10 μm to 1000 μm determined by the specific applications. Hence most of the currently available detectors for hard x-rays, including thin film transistor flat panel detector (TFT-FPO), charge-coupled device (CCD) detector, and complementary metal-oxide-semiconductor (CMOS) detector, can be used. Appropriate scintillators should be chosen for the best x-ray energy response. A higher frame rate is expected that makes it possible for faster scanning process and reduced motion artifacts.

Figure 7:
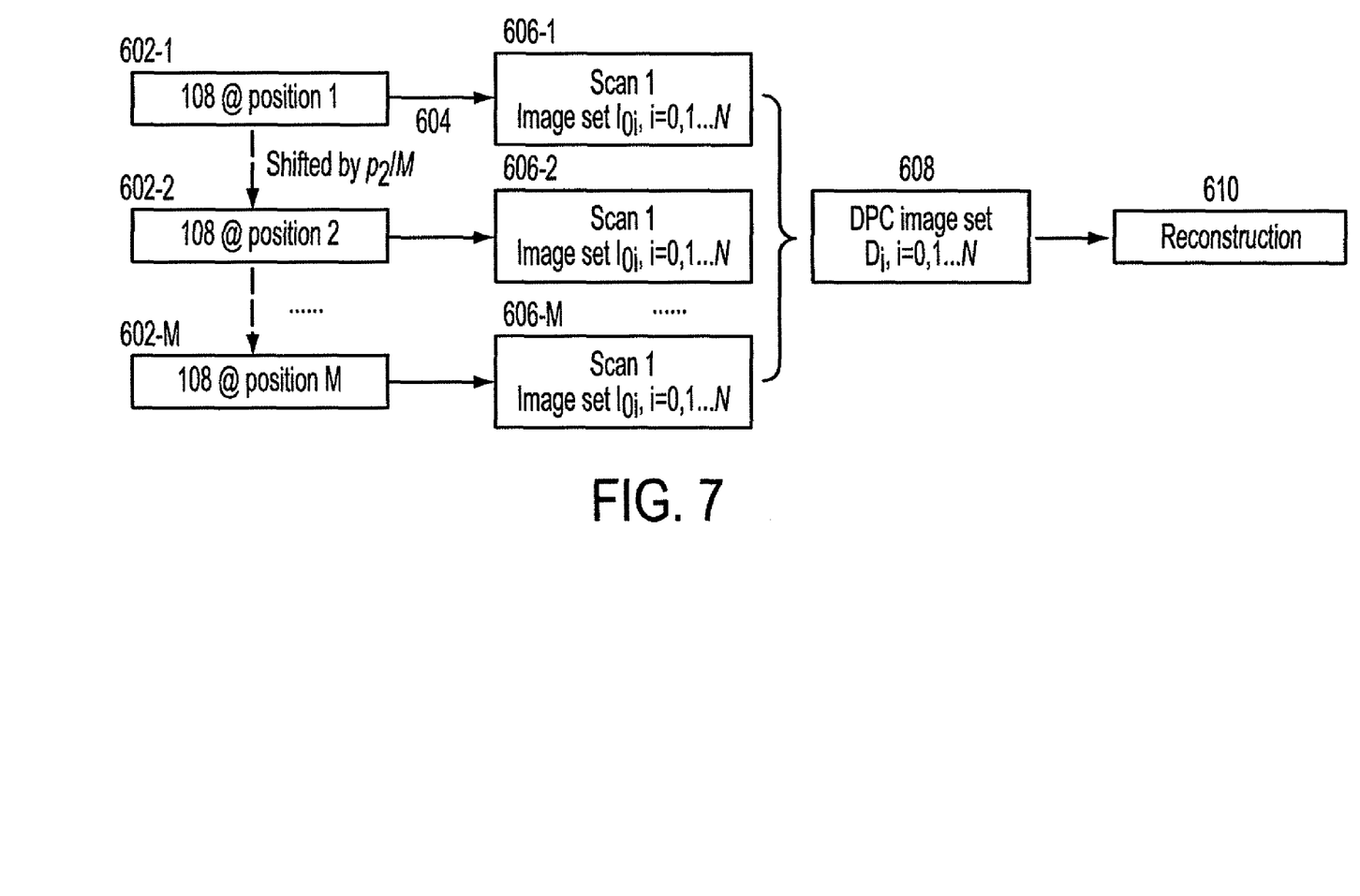
FIG. 7 is a flow chart showing a scanning protocol.

The conventional CBCT scanning protocol is quite straightforward, as only one x-ray exposure is needed to acquire an absorption image at each view angle. The DPC-CBCT technique, however, requires at least three x-ray exposures at any view angle, and the analyzer grating will be shifted to different position for each exposure to acquire the phase-stepping images, which will then be processed to compute the final DPC image at this view angle. Thus the phase-stepping algorithm for phase retrieval adds more complexity in the DPC-CBCT scanning protocols. We propose to divide a complete DPC-CBCT scan into several sub-scans, the analyzer grating being shifted before each sub-scan but fixed during each sub-scan. This will remove the positioning error due to repeated forward-backward movement of the analyzer grating. Then the phase-stepping algorithm will be performed to calculate the DPC images at each view angle, and the reconstruction algorithm will be performed to calculate the tomographic images. Assuming that M phase-stepping images (M≧3) are needed to calculate the DPC image at each view angle and N DPC images are needed for tomographic reconstruction, the whole scanning process is illustrated in FIG. 7. The analyzer grating 108 is positioned in a plurality of steps 602-1, 602-2, . . . , 602-M in a plurality of positions; between those steps, it is repositioned in step 604. When the analyzer grating is in each of the positions, a scanning step 606-1, 606-2, . . . , 606-M is performed to take an image set. The scans result in a DPC image set in step 608, which is reconstructed in step 610. Phase wrapping due to large phase derivatives or high noise level in intensity images is the major problem that may cause false phase information in DPC images, appearing as discontinuities. This problem will be solved by detecting singularities based on wavelet analysis and correcting singularities by interpolation.

High precision, good stability and accurate alignment are required in construction and calibration of the DPC-CBCT system, which concern mostly the relative position of the gratings 106 and 108. They should be mechanically stable with respect to one another down to a scale of approximately one-tenth of the analyzer grating period. The similar scale of stability also applies to the precision of transverse grating motion used in phase stepping method, and thus a linear stage with a precision of 0.1 μm (one-way) can be used. The back-and-forth movement will be avoided in phase stepping to eliminate the hysteresis error. The grating mounts will be equipped with precise one-way translation and three-way rotation to make the gratings 106 and 108 well aligned with their grooves parallel to each other. The angular sensitivity of grating mounts is expected to be within a couple milliradians to minimize a possible moiré pattern that occurs if the grooves are not well aligned. Also if the moiré pattern is not severe, it can be cancelled out by subtracting the background phase image. As the gantry will be rotated during a scan, it is a mechanical challenge to stably rotate the huge weight while keeping the relative position between the tube, the detector and the grating system unchanged with an accuracy of a few microns.

Large-scale fabrication techniques with silicon wafers are under development that are able to make gratings as large as 30 cm×30 cm. The advance of MEMS techniques may also make it possible to make two dimensional gratings that are able to show phase contrast equally well in both directions and eliminate the possible problems with object orientation. There are no major technical obstacles in fabrication of large-area (up to 50 cm×50 cm), high-resolution (>25 lp/mm) detectors using CMOS or CCD techniques, and the frame rate is expected to be improved by tens of times with novel parallel acquisition and fast caching techniques. Hence the field of view will be greatly enlarged for ultrahigh resolution breast imaging or whole body imaging. Though the x-ray tube is not a limitation for DPC imaging, emerging techniques of compact micro-focus x-ray tubes, including laser plasma tubes and liquid metal target tubes will further improve image resolution and simplify the system design by removing the grating 104 that may increase field of view and improve exposure uniformity.

With the technique advances described above, the DPC-CBCT imaging system is expected to scan faster (achieve a few seconds/scan), cover larger objects, and provide higher spatial resolution, which makes it possible to use the DPC-CBCT imaging as both screening and diagnosis tools. The screening DPC-CBCT system will be designed with a lower spatial resolution (~100-75 μm) and the patient will be exposed with very low exposure (lower than that of two view screening mammography). The diagnostic DPC-CBCT system will be designed with a higher spatial resolution (~50-20 μm) and the patient dose will be equivalent to that of a diagnostic mammography (~6 mGy for average size normal density breast). Currently the VOI breast imaging is designed as a hybrid system with two sub-systems: a CBCT system and a DPC-CBCT system. In the future it can be further simplified as a single DPC-CBCT imaging system that can perform both a screening scan and a diagnostic VOI scan by switching the field of view, different resolutions (standard resolution for large field view and screening imaging and ultrahigh resolution for small field and diagnostic imaging) and different readout rates (0.5 frame/s-120 frame/second).

Figure 8:
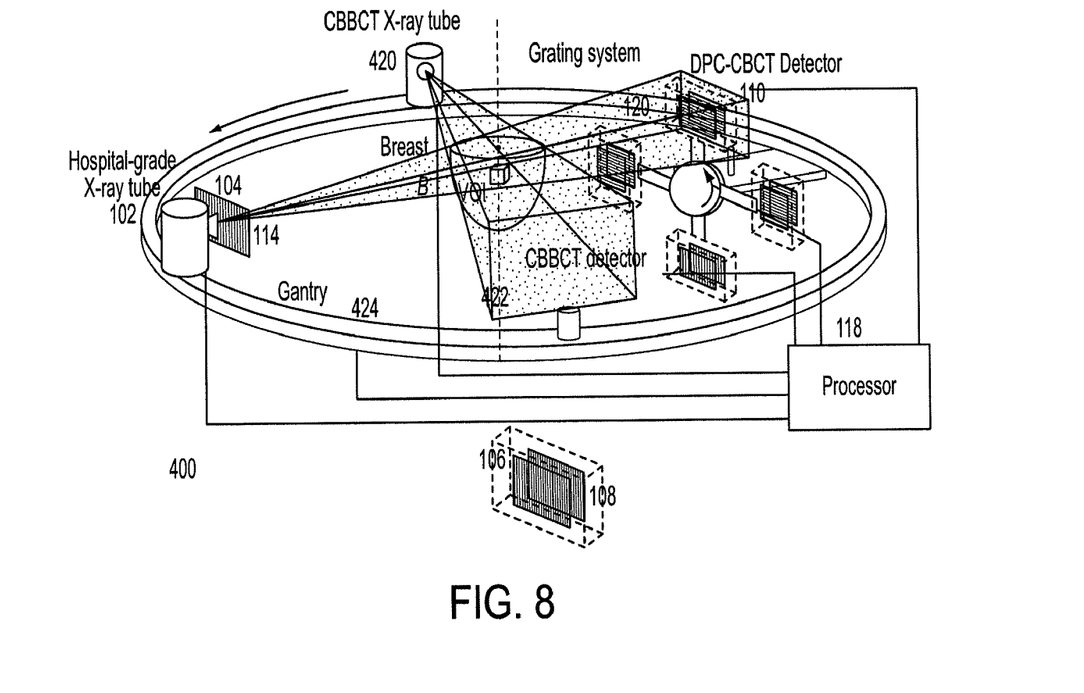
FIG. 8 is a schematic diagram showing a system according to a fourth preferred embodiment.

Our first application of the proposed DPC-CBCT technique is a cone beam breast CT modality for breast cancer diagnosis to reduce the biopsy rate, while this technology can be also used for whole body imaging as well as angiography and bone imaging. A fourth preferred embodiment combines current cone beam CT with DPC-cone-beam CT to form a hybrid cone beam CT that is capable of acquiring both 3D high resolution cone beam CT imaging and ultrahigh resolution DPC-cone-beam CT imaging. FIG. 8 shows one possible design for a hybrid cone-beam CT system 400 for breast imaging. The system 400 includes a current cone beam breast CT (CBBCT) system, which is mainly composed of an x-ray tube 420 and a flat-panel detector 422. On the same rotary gantry 424, a DPC-CBCT system is constructed which is mainly composed of an x-ray tube 102, a high-resolution detector 110 and a grating system, which are described above. The CBBCT is used to scan the whole breast B first and find out the 3D location of any suspicious volume; the breast is then translated and positioned such that the suspicious volume is centered in the field of view (FOV) of the DPC-CBCT system; finally the DPC-CBCT system performs an ultrahigh-resolution scan of a region of interest (ROI), and the phase coefficient of the 3D volume is reconstructed. This ultrahigh-resolution DPC-CBCT scan is expected to reveal ducts (<0.25 mm in width), small vessels (<0.5 mm in width) and microcalcifications (<0.2 mm in diameter) for diagnosis and treatment of breast cancers.

Figure 9A:
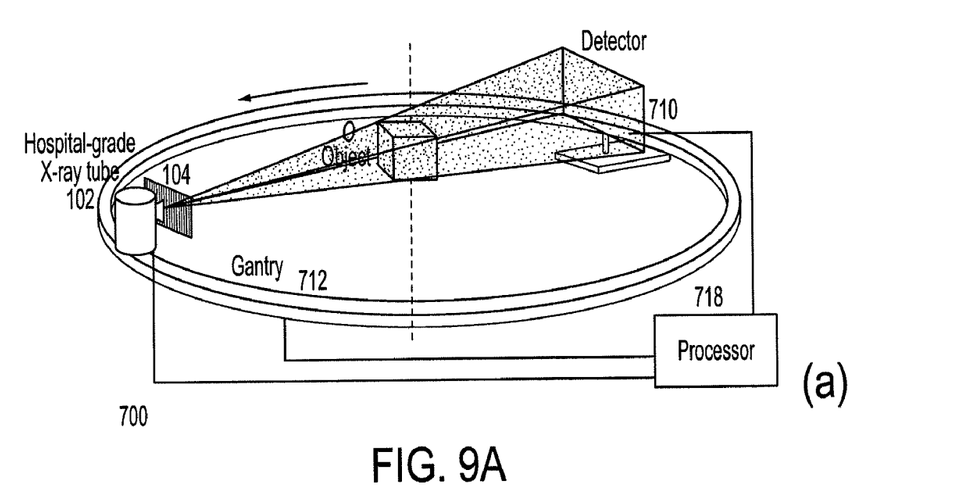
FIGS. 9A and 9B are schematic diagrams showing a system according to a fifth preferred embodiment.
Figure 9B:
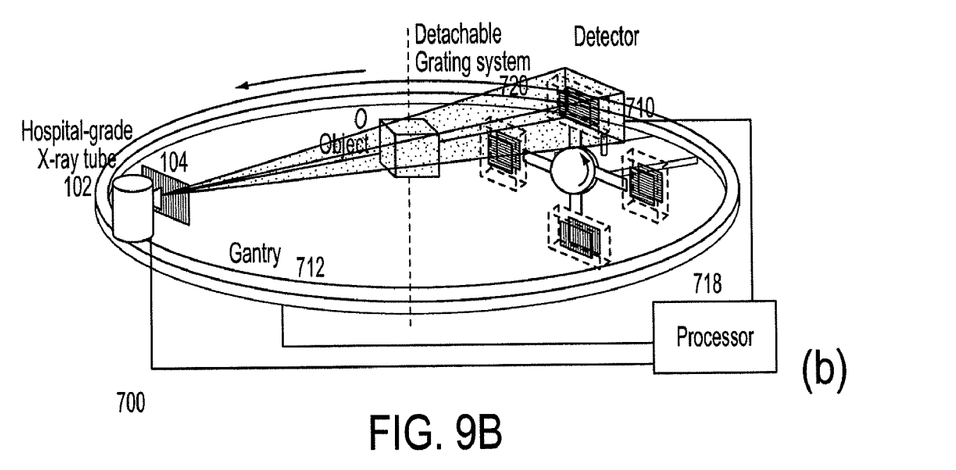

The fifth preferred embodiment is a variation of the hybrid system as shown in FIGS. 9A and 9B, where there is only one imaging chain and the grating system 720 is designed as a detachable unit. The detector can be a high resolution detector with a pitch of 150 μm-1000 μm. When the grating system 720 is unmounted as shown in FIG. 9A, a conventional CBCT imaging scan can be performed. It should be noted that the source grating 104 does not have to be unmounted for this purpose as it would not noticeably influence the imaging process because each line source is much smaller compared to the focal spot size. When the grating system 720 is mounted, the system is able to perform a DPC-CBCT scan as described for the first preferred embodiment to achieve much higher contrast resolution at the same spatial resolution. It is straightforward that a micro-focus tube can be used without using the source grating because a micro-focus tube is ideal for DPC-CBCT as described for the second preferred embodiment and it is good for conventional CBCT imaging.

Figure 10:
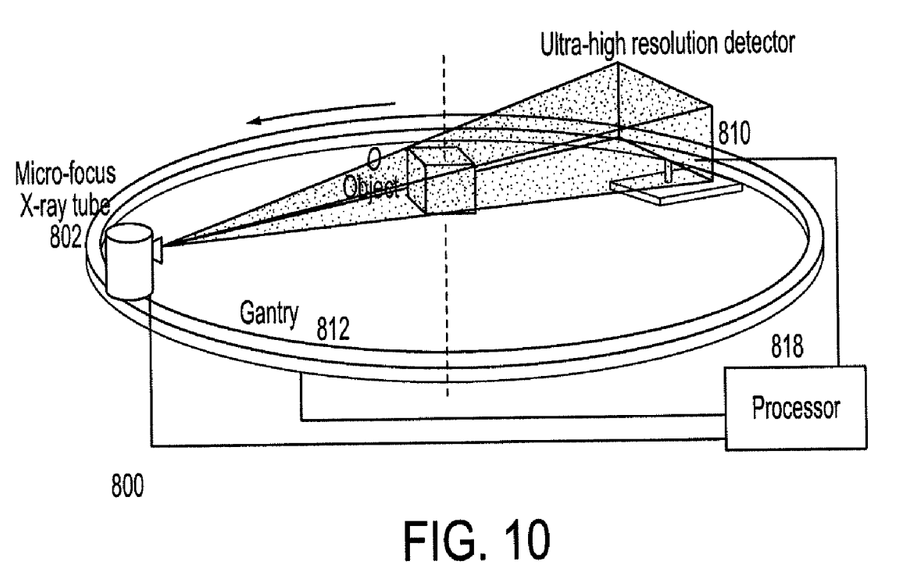
FIG. 10 is a schematic diagram showing a system according to a sixth preferred embodiment.

The idea of hybrid CBCT system can be implemented for in-line phase-contrast imaging as well where no grating system is present and it becomes the sixth preferred embodiment as shown in FIG. 10. The x-ray source is a micro-focus x-ray tube with a focal spot size less than 50 μm, being able to generate partially coherent x-rays. An ultra-high resolution detector with a pitch less than 70 μm is used, and multiple rebinning modes are available for image acquisition. In a higher rebinning mode that has a effective pitch of >150 μm, the conventional CBCT scan can be performed, while in a 1×1 rebinning mode that has the highest spatial resolution, an in-line phase-contrast CBCT scan can be performed as the edge-enhancement can be captured with such a high resolution.

It should be noted that all the five embodiments can be performed in a spiral scan mode to increase the coverage by moving the object along the rotation axis while the gantry is rotating. There are no theoretical or mechanical difficulties for this application extension.

While preferred embodiments and variations thereon have been disclosed above, those skilled in the art who have reviewed the present disclosure will readily appreciate that other embodiments can be realized within the scope of the invention. For example, numerical values are illustrative rather than limiting. Also, any suitable technique or materials for manufacturing the grating can be used. Furthermore, the utility of the present invention is not limited to breast imaging, but instead can be applied to any biological or non-biological imaging. Therefore, the present invention should be construed as limited only by the appended claims.

We claim:

1. A device for imaging an object, the device comprising:
a gantry frame;
at least one motor for moving the gantry frame for a data acquisition geometry;
an x-ray source disposed on the gantry frame to be on a first side of the object;

a grating system disposed on the gantry;

said grating system comprising a phase grating, so that x-rays from the x-ray source which have passed through the object pass through the phase grating;

said grating system further comprising an analyzer grating, so that x-rays which have passed through the phase grating pass through the analyzer grating;

an x-ray detector on the gantry frame, disposed so that x-rays which have passed through the analyzer grating are incident on the x-ray detector, for producing a signal in response to the x-rays which are incident on the x-ray detector; and a computer system, in communication with the gantry, x-ray source, the grating system and the detector, for controlling the gantry motion, x-ray emission, and grating system movement and for analyzing the signal from the x-ray detector to image the object;

wherein the grating system is configured to produce a plurality of phase steps, and wherein the computer system is configured such that an intensity image is acquired for each phase step, from which a differential phase-contrast (DPC) image is calculated using the phase stepping algorithm; both background DPC images and object DPC images are obtained, and the background DPC image is subtracted from the object DPC image to generate the subtracted DPC images for reconstruction; and wherein the gantry, controlled by the computer system, moves the x-ray source, the grating system and the detector around the object to take a plurality of subtracted DPC images at different view angles, performing three-dimensional (3D) cone beam reconstruction in the computer system from the subtracted DPC images, outputting a 3D reconstruction matrix of a distribution of linear phase coefficient in accordance with the 3D reconstruction, and generating images from the 3D matrix in the computer system.

2. The device of claim 1, wherein the x-ray source comprises:
   a cone-beam x-ray source for emitting a cone beam of x-ray radiation; and
   a source grating for dividing the cone beam into the plurality of x-ray line sources or point sources.

3. The device of claim 2, wherein the source grating comprises a line pattern of a substance which is opaque to x-ray photons from the x-ray source.

4. The device of claim 3, wherein the substance comprises gold or other high atomic number material.

5. The device of claim 1, wherein the x-ray source comprises a micro-focus x-ray source.

6. The device of claim 1, wherein the x-ray source comprises a collimator to obtain a fan-shaped x-ray beam.

7. The device of claim 1, wherein the grating system has a plurality of branches where each branch has a grating set of a phase grating and an analyzer grating that are configured to function as a shearing interferometer.

8. The device of claim 7, wherein the relative displacement between the phase grating and the analyzer grating in each branch of the grating system correspond to a successive set of phase steps.

9. The device of claim 7, wherein the grating system, controlled by the computer system, rotates and successively aligns the grating set on each branch with the optical axis to acquire a plurality of intensity images, from which a DPC image is calculated using the phase-stepping algorithm.

10. The device of claim 1, wherein the grating system has one phase grating, one analyzer grating and a linear stage that carries either of the gratings to produce a plurality of phase steps, and intensity images are taken at different phase steps, from which a DPC image is calculated using the phase-stepping algorithm.

11. The device of claim 1, wherein the phase grating and the analyzer grating are separated by a fractional or integer Talbot distance.

12. The device of claim 1, wherein the analyzer grating has a period which is equal to a period of fringes produced by the phase grating at said fractional or integer Talbot distance.

13. The device of claim 1, further comprising a second x-ray source and a second x-ray detector, both mounted on said gantry frame, for performing cone-beam computed tomography on the object.

14. The device of claim 13, wherein the processor is programmed to perform said cone-beam computed tomography on the object using the second x-ray source and the second x-ray detector to locate a volume of interest and then to use the x-ray source, grating system and the x-ray detector to perform said DPC-CBCT scans to image the volume of interest.

15. The device of claim 1, wherein the grating system is detachable.

16. The device of claim 15, wherein a conventional CBCT scan can be performed when the grating system is unmounted and a DPC-CBCT scan can be performed when the grating system is mounted.

17. The device of claim 1, wherein the data acquisition geometry is a circle geometry.

18. The device of claim 1, wherein the data acquisition geometry is a spiral geometry.

19. The device of claim 1, wherein the data acquisition geometry is a circle-plus-line geometry.

20. The device of claim 19, wherein the circle-plus-line geometry comprises a single line.

21. The device of claim 19, wherein the circle-plus-line geometry comprises a plurality of lines.

22. The device of claim 1, wherein the data acquisition geometry is a 180° plus cone angle circle scan.

23. The device of claim 1, wherein the data acquisition geometry is a 360° scan.

24. The device of claim 1, wherein the reconstruction algorithm is a filtered backprojection algorithm.

25. The device of claim 24, wherein the filter kernel is a Hilbert filter.

26. The device of claim 1, wherein the reconstruction algorithm is a backprojection filtration algorithm.

27. The device of claim 1, wherein both background DPC images and DPC images with object in place are obtained using the phase-stepping algorithm.

28. The device of claim 27, wherein the background DPC images are acquired without object in place and can be pre-stored for background correction.

29. The device of claim 1, wherein the object DPC images are corrected by directly subtracting the background DPC image.

30. The device of claim 1, wherein the phase-stepping algorithm comprises:
   (a) for each pixel, grouping as an array the values of this pixel at all the intensity images taken at all phase steps;
   (b) calculating the Fourier transform of the array;
   (c) taking the phase of the first Fourier component as the DPC value at the corresponding pixel; and
   (d) repeating the process for each pixel to generate a DPC image.

31. The device of claim 1, wherein the source grating, phase grating and analyzer grating of the grating system are two-dimensional gratings.

32. A device for imaging an object, the device comprising:
a gantry frame;
at least one motor for moving the gantry frame for a data acquisition geometry;
an x-ray source disposed on the gantry frame to be on a first side of the object;
an x-ray detector on the gantry frame, disposed so that x-rays which have passed through the object are incident on the x-ray detector, for producing a signal in response to the x-rays which are incident on the x-ray detector; and
a computer system, in communication with the gantry, x-ray source and the detector, for controlling the gantry motion, x-ray emission and for analyzing the signal from the x-ray detector to image the object;
wherein the x-ray source is a micro-focus x-ray source;
wherein the detector is a ultra-high resolution detector with multiple rebinning modes; and
wherein the gantry, controlled by the computer system, moves the x-ray source and the detector around the object to take a plurality of intensity images at different view angles, performing three-dimensional (3D) cone beam reconstruction in the computer system from the intensity images, outputting a 3D reconstruction matrix of a distribution of linear phase coefficient or linear attenuation coefficient in accordance with the 3D reconstruction, and generating images from the 3D matrix in the computer system.

33. The device of claim 32, wherein a conventional CBCT scan can be performed with a lower detector resolution mode and an in-line CBCT scan can be performed with a ultra-high resolution mode.

34. A method for imaging an object, the method comprising:
(a) causing x-rays to be incident on the object;
(b) causing x-rays which have passed through the object to pass through a grating system which comprises a phase grating and an analyzer grating such that the x-rays which have passed through the object pass through the phase grating and the analyzer grating;
(c) detecting x-rays which have passed through the grating system to produce a signal;
(d) operating the grating system to perform a phase-stepping algorithm and acquire a plurality of signals;
(e) analyzing the signal to form a DPC image using the phase-stepping algorithm;
(f) moving the radiation source, the grating system and the detector around the object under control of a computer to take a plurality of said DPC images at different view angles;
(g) performing 3D cone beam reconstruction in the computer from the DPC images;
(h) outputting a 3D reconstruction matrix of the distribution of linear phase coefficient in accordance with the 3D reconstruction; and
(i) generating images from the 3D matrix in the computer;
wherein step (f) comprises moving the cone-beam radiation source and the detector to define a data acquisition geometry; and
wherein step (g) comprises taking both background DPC images and object DPC images, and subtracting the background DPC image from the object DPC image to generate subtracted DPC images for reconstruction.

35. The method of claim 34, wherein step (a) comprises:
(i) emitting a cone beam of x-ray radiation from a cone-beam x-ray source; and
(ii) dividing the cone beam into the plurality of x-ray line sources using a source grating.

36. The method of claim 35, wherein the source grating comprises a line pattern of a substance which is opaque to x-ray photons from the x-ray source.

37. The method of claim 36, wherein the substance comprises gold or other high atomic number materials.

38. The method of claim 34, wherein the x-ray source comprises a micro-focus x-ray source.

39. The method of claim 34, wherein the x-ray source comprises a collimator to obtain a fan-shaped x-ray beam.

40. The method of claim 34, wherein the grating system has a plurality of branches where each branch has a grating set of a phase grating and an analyzer grating that are configured to function as a shearing interferometer.

41. The method of claim 40, wherein the relative displacement between the phase grating and the analyzer grating in each branch of the grating system corresponds to a successive set of phase steps.

42. The method of claim 40, wherein the grating system rotates and successively aligns the grating set on each branch with the optical axis to acquire a plurality of intensity images, from which a DPC image is calculated using the phase-stepping algorithm.

43. The method of claim 34, wherein the grating system has one phase grating, one analyzer grating and a linear stage that carries either of the gratings to produce a plurality of phase steps, and intensity images are taken at different phase steps, from which a DPC image is calculated using the phase-stepping algorithm.

44. The method of claim 34, wherein the phase grating and the analyzer grating are separated by a fractional or integer Talbot distance.

45. The device of claim 34, wherein the analyzer grating has a period which is equal to a period of fringes produced by the phase grating at said fractional or integer Talbot distance.

46. The method of claim 34, further comprising performing cone-beam computed tomography on the object.

47. The method of claim 46, wherein said cone-beam computed tomography is performed on the object using the second x-ray source and the second x-ray detector to locate a volume of interest, and then steps (a)-(i) are performed on the volume of interest.

48. The method of claim 47, wherein the grating system is detachable and said cone beam computed tomography is performed when the grating system is unmounted.

49. The method of claim 34, wherein the data acquisition geometry is a circle geometry.

50. The method of claim 34, wherein the data acquisition geometry is a spiral geometry.

51. The method of claim 34, wherein the data acquisition geometry is a circle-plus-line geometry.

52. The method of claim 51, wherein the circle-plus-line geometry comprises a single line.

53. The method of claim 51, wherein the circle-plus-line geometry comprises a plurality of lines.

54. The method of claim 34, wherein the data acquisition geometry is a 180° plus cone angle circle scan.

55. The method of claim 34, wherein the data acquisition geometry is a 360° scan.

56. The method of claim 34, wherein the reconstruction algorithm is a filtered backprojection algorithm.

57. The method of claim 56, wherein the filter kernel is a Hilbert filter.

58. The method of claim 34, wherein the reconstruction algorithm is a backprojection filtration algorithm.

59. The method of claim 34, wherein both background DPC images and DPC images with object in place are obtained using the phase-stepping algorithm.

60. The method of claim 59, wherein the background DPC images are acquired without object in place and can be pre-stored for background correction.

61. The method of claim 34, wherein the phase-stepping algorithm comprises:
(i) for each pixel, grouping as an array the values of this pixel at all the intensity images taken at all phase steps;
(ii) calculating the Fourier transform of the array;
(iii) taking the phase of the first Fourier component as the DPC value at the corresponding pixel; and
(iv) repeating the process for each pixel to generate a DPC image.

62. The method of claim 34, wherein the source grating, phase grating and analyzer grating of the grating system are two-dimensional gratings.

* * * * *